(12) United States Patent
Blake et al.

(10) Patent No.: US 10,487,968 B2
(45) Date of Patent: Nov. 26, 2019

(54) LOCKING FLUID CONNECTOR

(71) Applicant: SARTORIUS STEDIM FMT SAS, Aubagne (FR)

(72) Inventors: Florian Blake, Hyeres (FR); Jeremy Gibelin, Le Beausset (FR)

(73) Assignee: SARTORIUS STEDIM FMT SAS, Aubagne (FR)

( * ) Notice: Subject to any disclaimer, the term of this patent is extended or adjusted under 35 U.S.C. 154(b) by 535 days.

(21) Appl. No.: 14/901,582

(22) PCT Filed: Jun. 25, 2014

(86) PCT No.: PCT/FR2014/051601
§ 371 (c)(1),
(2) Date: Dec. 28, 2015

(87) PCT Pub. No.: WO2014/207382
PCT Pub. Date: Dec. 31, 2014

(65) Prior Publication Data
US 2016/0369922 A1 Dec. 22, 2016

(30) Foreign Application Priority Data
Jun. 28, 2013 (FR) .................................. 13 56352

(51) Int. Cl.
*F16L 37/098* (2006.01)
*A61M 39/10* (2006.01)
(Continued)

(52) U.S. Cl.
CPC ......... *F16L 37/0987* (2013.01); *A61J 1/1481* (2015.05); *A61M 39/1011* (2013.01);
(Continued)

(58) Field of Classification Search
CPC ............ F16L 37/0985; A61M 39/1011; A61M 2039/1027
(Continued)

(56) References Cited

U.S. PATENT DOCUMENTS 4,219,222 A * 8/1980 Brusadin ............. F16L 37/0985
285/315
4,660,803 A * 4/1987 Johnston ............. F16L 37/0985
137/533.17
(Continued)

FOREIGN PATENT DOCUMENTS

CA 2250672 A1 * 4/2000 .......... F16L 25/0045
DE 203 21 171 U1 4/2006
(Continued)

OTHER PUBLICATIONS

International Search Report, dated Oct. 22, 2014, from corresponding PCT application.

*Primary Examiner* — David Bochna
(74) *Attorney, Agent, or Firm* — Young & Thompson

(57) ABSTRACT

Disclosed is a fluid-connection device for connecting a first wall defining a first fluid space, for example a flexible pipe, to a second wall defining a second fluid space, in the form of a flexible pipe or enclosure, including a first male connector, the first connector including a seal and a snap-fitting collar, the seal extending radially prior to coupling from the axis until a first radial distance R1, a second female connector capable of receiving the first connector, the second connector including at least one flexible tab with one end against which the locking collar abuts in coupling position, in order to prevent retraction from the coupling position, the flexible tab being defined relative to the axis between a second radial distance R2 and a third radial distance R3, which is greater than the second radial distance R2, wherein R2>R1.

18 Claims, 5 Drawing Sheets

(51) Int. Cl.
  *F16L 33/025* (2006.01)
  *A61J 1/14* (2006.01)

(52) U.S. Cl.
  CPC ......... *F16L 33/025* (2013.01); *A61J 2205/60* (2013.01); *A61M 2039/1027* (2013.01); *F16L 2201/10* (2013.01); *F16L 2201/44* (2013.01); *F16L 2201/60* (2013.01)

(58) Field of Classification Search
  USPC .................................................. 285/305, 308
  See application file for complete search history.

(56) References Cited

U.S. PATENT DOCUMENTS

| | | | | |
|---|---|---|---|---|
| 4,673,200 A | * | 6/1987 | Miyauchi | F16L 37/0985 |
| | | | | 285/319 |
| 4,923,228 A | * | 5/1990 | Laipply | F16L 37/0982 |
| | | | | 285/319 |
| 4,969,879 A | * | 11/1990 | Lichte | F16L 37/0985 |
| | | | | 285/319 |
| 5,123,677 A | * | 6/1992 | Kreczko | F16L 37/0985 |
| | | | | 285/24 |
| 5,799,986 A | * | 9/1998 | Corbett | B29C 45/1671 |
| | | | | 285/305 |
| 5,873,610 A | * | 2/1999 | Szabo | F16L 37/0987 |
| | | | | 285/308 |
| 5,984,378 A | * | 11/1999 | Ostrander | F16L 37/0985 |
| | | | | 285/319 |
| 7,690,694 B2 | * | 4/2010 | Poder | F16L 37/0985 |
| | | | | 285/308 |
| 8,029,024 B2 | | 10/2011 | Guest | |
| 2002/0070549 A1 | * | 6/2002 | Romero | F16L 37/0987 |
| | | | | 285/305 |
| 2003/0146622 A1 | * | 8/2003 | Youssefifar | F16L 25/0045 |
| | | | | 285/305 |
| 2003/0146626 A1 | * | 8/2003 | Youssefifar | F16L 25/0045 |
| | | | | 285/305 |
| 2005/0016620 A1 | * | 1/2005 | Proulx | A61M 39/10 |
| | | | | 141/27 |
| 2005/0082828 A1 | * | 4/2005 | Wicks | F16L 37/098 |
| | | | | 285/319 |

FOREIGN PATENT DOCUMENTS

| | | |
|---|---|---|
| EP | 1 457 727 A2 | 9/2004 |
| WO | 2005/073613 A1 | 8/2005 |
| WO | 2007/013813 A1 | 2/2007 |

\* cited by examiner

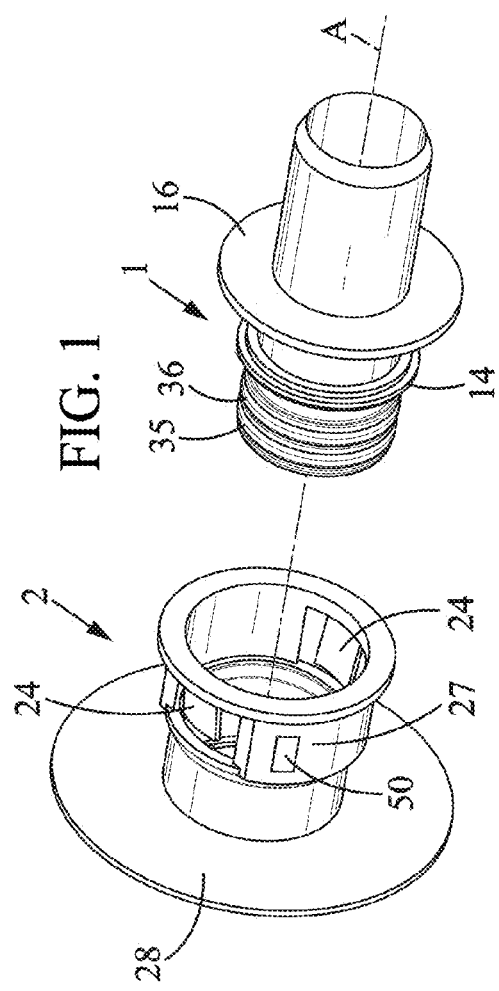
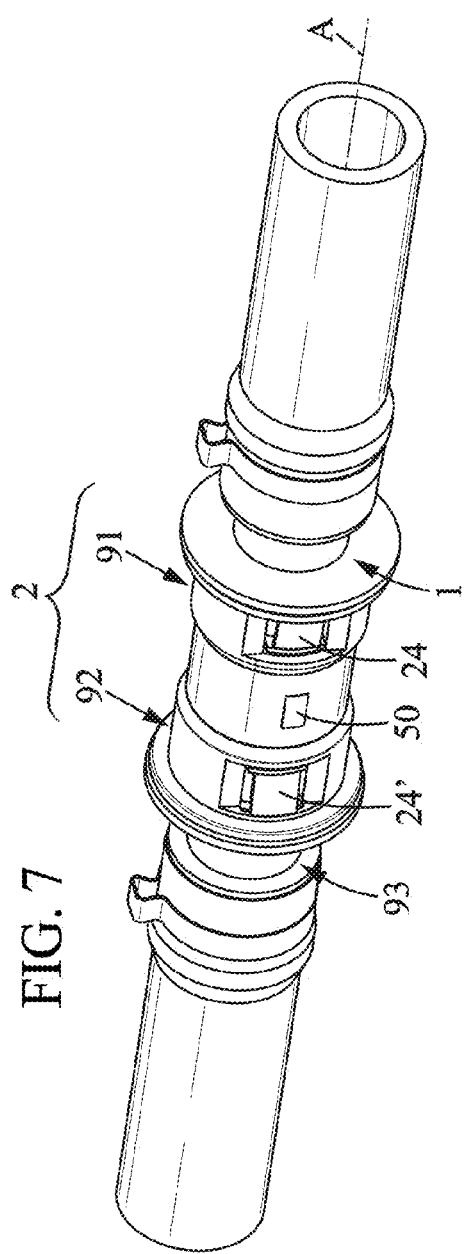

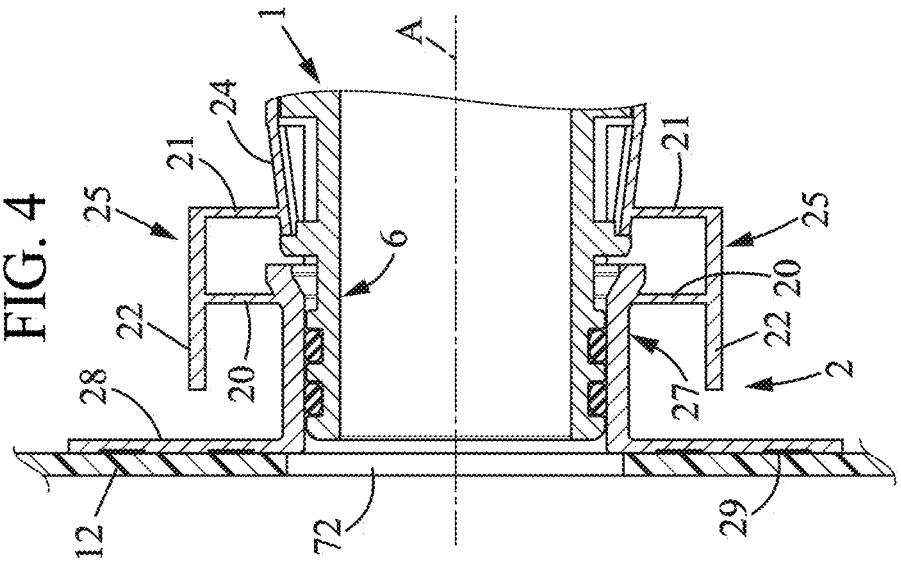
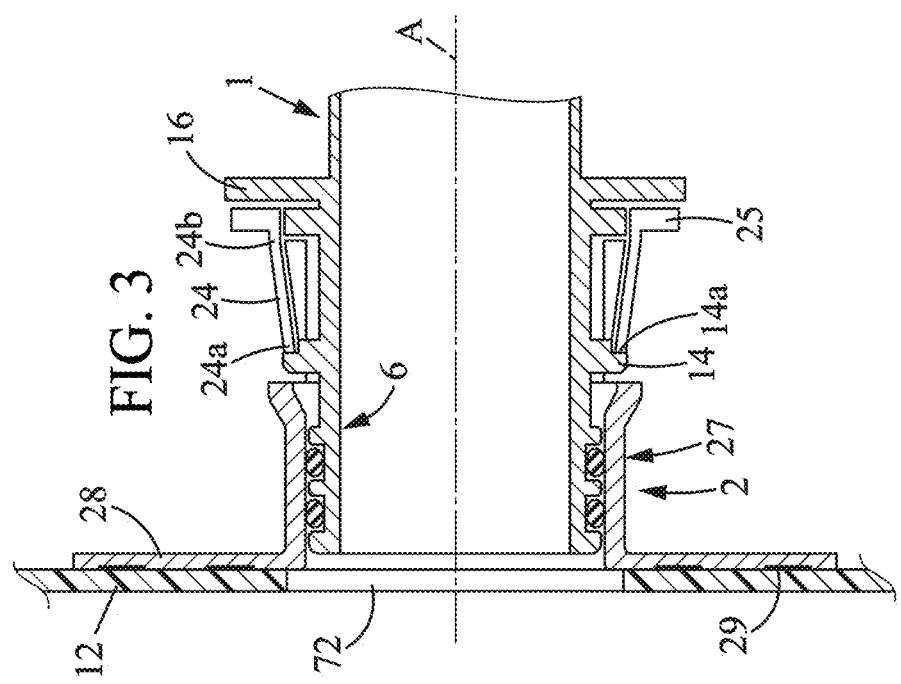

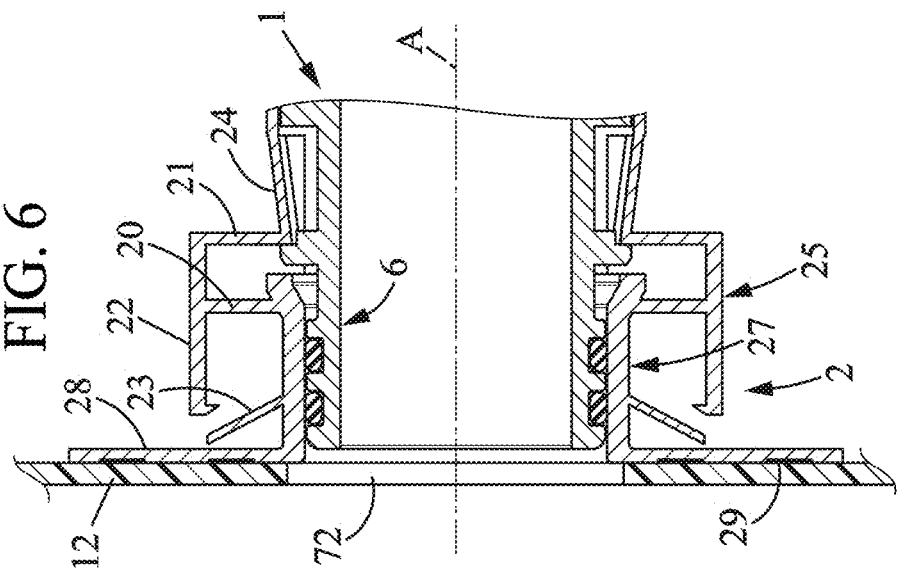
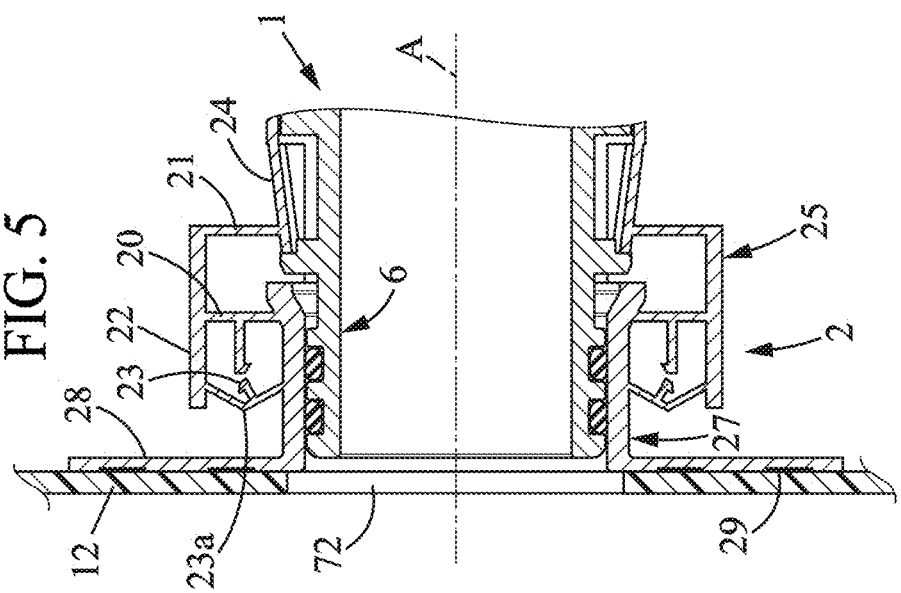

LOCKING FLUID CONNECTOR

FIELD OF THE INVENTION

The invention relates to fluid connections, in particular fluid connections for coupling a fluid-conveying pipe to another pipe or to a container, in the field of biopharmaceutical applications.

BACKGROUND OF THE INVENTION

Specifically, the tubes or pipes used in the biopharmaceutical field are flexible pipes which are used to convey various biopharmaceutical substances, most often with the aseptic precautions required. In biopharmaceutical applications, this type of flexible pipe allows the circulation, passage, and communication of a fluid such as a biopharmaceutical fluid, and can be connected by means of a fluid connection either to a similar flexible pipe or to a vessel or container which may be rigid or flexible.

This vessel or container may be a flexible or semi-rigid bag, a rigid enclosure, a filter or filter cartridge, or any other device used in a biopharmaceutical assembly.

In a typical embodiment, for example, the fluid connections have an internal working diameter of between for example 4 millimeters and 30 millimeters.

In fluid connections between pipes, bags, enclosures, filter cartridges, and other biopharmaceutical devices, it is very common to use "quick" connections where a male connector is mated with a female connector. The connectors in question are usually made of plastic.

In order to ensure good performance in terms of fluid-tightness while considering manufacturing variations and the various admissible tolerances, it is usual to install one or more seals between the male part and the female part. In practice, an O-ring placed in an annular groove is often used.

It is easier to create such a groove in the male part (outer groove) than in the female part (inner groove), and therefore it is advantageous to have the O-ring in an annular groove on the male endpiece.

It is advantageous to provide a locking connection between the female connector and male connector to prevent unwanted or inadvertent detachment of the male-female connection. Conventionally, this locking is obtained by snap-fitting means. In practice, it is preferred to provide these snap-fitting means in integrated form, by the engagement of cooperating shapes of the female connector and male connector, as is disclosed in document U.S. Pat. No. 8,029,024.

To facilitate obtaining the plastic parts concerned, often there is at least one resilient tab in the female part, this resilient tab being pushed outward by the passage of the male endpiece toward the coupling position; the resilient tab then returns to a rest position where it abuts against an abutment surface that is part of the male connector, in the coupling position.

In addition, this configuration helps secure the snap-fit, as the flexible tabs must be spread apart in order to unlock the connection, which is more difficult to achieve than bringing the flexible tabs back toward the center (which would be the case if the flexible tabs were arranged on the male connector).

Another constraint lies in the requirement for a radially compact male-female coupling solution with its snap-fitting device; in particular the total radial footprint for a given internal working diameter of the fluid connection must be kept small.

However, in the above configuration, during the movement of inserting the male connector into the female connector, the free end of the flexible tab can interfere with the outer surface of the seal as the seal advances, which can damage the seal for example by scratching it.

There is therefore a need to propose an improvement that at least partially overcomes one of the aforesaid disadvantages of the known prior art.

OBJECTS AND SUMMARY OF THE INVENTION

A description of the invention as characterized in the claims is provided below.

According to a first aspect, the invention relates to a fluid-connection device adapted and intended for connecting a first wall defining a first fluid space to a second wall defining a second fluid space, in a biopharmaceutical assembly, so as to ensure a fluid communication between the first fluid space and the second fluid space, comprising:

a first connector, defining a first hollow passage, adapted and intended for connection to the first wall and in fluid communication with the first fluid space, the first connector being of the male type, the first connector comprising at least one seal and a snap-fitting collar, the seal extending radially from the axis to a first radial distance R1, this first distance being measured before coupling when the seal is mounted on the first connector, a second connector defining a second hollow passage, adapted and intended for connection to the second wall and in fluid communication with the second fluid space, the second connector being of the female type, the first connector and the second connector being adapted and intended to be coupled together in a relative coupling position, along an axis A, the second connector comprising at least one flexible tab with at least one free end against which the locking collar abuts when in the coupling position, to prevent withdrawal from the coupling position, the free end of the flexible tongue being distanced from the axis, at rest, by a second radial distance R2, wherein R2>R1, namely the second radial distance R2 is greater than the first radial distance R1.

In this manner, there is no risk of the flexible tongue damaging the O-ring during insertion, ensuring optimum sealing by the O-ring.

In one embodiment, each of the flexible tongues has a free end oriented toward the second fluid space. The flexible tongues are thus protected, by the front portion of the second connector, from mechanical damage that could occur before coupling or during the coupling operation.

In one embodiment, the flexible tongue is circumscribed, relative to the axis, between the second radial distance R2 and a third radial distance R3 which satisfies the relation $1<R3/R2<1.4$.

The radial dimensions of the female connector thus remain very small.

In one embodiment, the snap-fitting collar has a maximum radial extension, denoted R6, which satisfies the relation $1<R6/R2<1.3$.

The radial dimensions of the male connector thus remain very small.

According to one embodiment, there are two diametrically opposed flexible tabs.

This provides a solution that is balanced, symmetrical, and particularly simple.

According to one embodiment, there are two O-rings between the front end of the first connector and the collar; this increases the level of fluid-tightness obtained.

In one embodiment, the seal is an O-ring or a lip seal of elastomeric material. The seal can thus be compressed in the coupling position to provide good sealing performance. In addition, it can deform during the insertion movement when coupling.

In one embodiment, each flexible tab is connected to an unlocking member integrally obtained when molding the second connector and which comprises a connecting member joined to the flexible tab, a bearing area, a radial arm arranged between the connecting member and the bearing area, the bearing area being intended to be pressed radially inward to urge the flexible tab radially outward and thereby release the locking collar.

This arrangement provides the possibility of unlocking the locking tongue and therefore of disconnecting the first and second connectors.

In one embodiment, the unlocking member comprises a secondary locking means for the bearing area, to prevent radially inward movement of the bearing area, thus doubly locking the connection.

A secondary lock is thus obtained which secures the primary lock. Advantageously, removal of the secondary lock results in visible damage to serve as an indicator of a disconnection attempt.

In one embodiment, the secondary locking means is a radially-oriented finger which is movable between an inactive position and an active position.

This represents a simple solution for the secondary lock.

In one embodiment, the secondary locking means forms an indicator of an unlocking attempt and may comprise a mechanical fuse region.

Any attempt to undo the secondary lock will break the mechanical fuse region and will be a lasting visible indicator of the unlocking attempt.

In one embodiment, the second connector comprises an additional auxiliary interface of the female type, formed symmetrically with respect to the first female-type interface, said auxiliary interface being configured to receive a third connector of the male type.

The second connector thus forms a double female connector that enables connecting two male connectors.

In one embodiment, the collar comprises an anti-rotation lug which extends radially beyond the rest of the collar. Relative rotation can thus be prevented between the first and second connector when in the coupling position.

In one embodiment, the first connector or the second connector further comprises an identifier such as a barcode or RFID tag or color code, whereby it is easy to access information concerning the flexible bag and/or the biopharmaceutical product contained therein, in particular to contribute to the traceability function.

According to a second aspect, the invention relates to a biopharmaceutical assembly comprising a fluid-connection device as described above.

According to a third aspect, the invention also provides a kit of parts comprising the first connector and the second connector described above. In addition, the invention relates to an assembly of the above parts into an assembled state.

BRIEF DESCRIPTION OF THE DRAWINGS

The figures in the drawings will now be briefly described.

FIG. 1 is an exploded view of a connection device according to the invention.

FIG. 3 is an axial sectional view of the connection device of FIG. 1, in the coupled position.

FIGS. 4, 5, and 6 are similar to FIG. 3 and show variants of the connection device, illustrating an unlocking member and a secondary lock.

FIG. 7 illustrates a variant of the connection device which enables connecting a male connector by means of a double female connector.

MORE DETAILED DESCRIPTION

A detailed presentation of an embodiment of the invention is provided below, accompanied by examples and with reference to the drawings.

Figure 2:
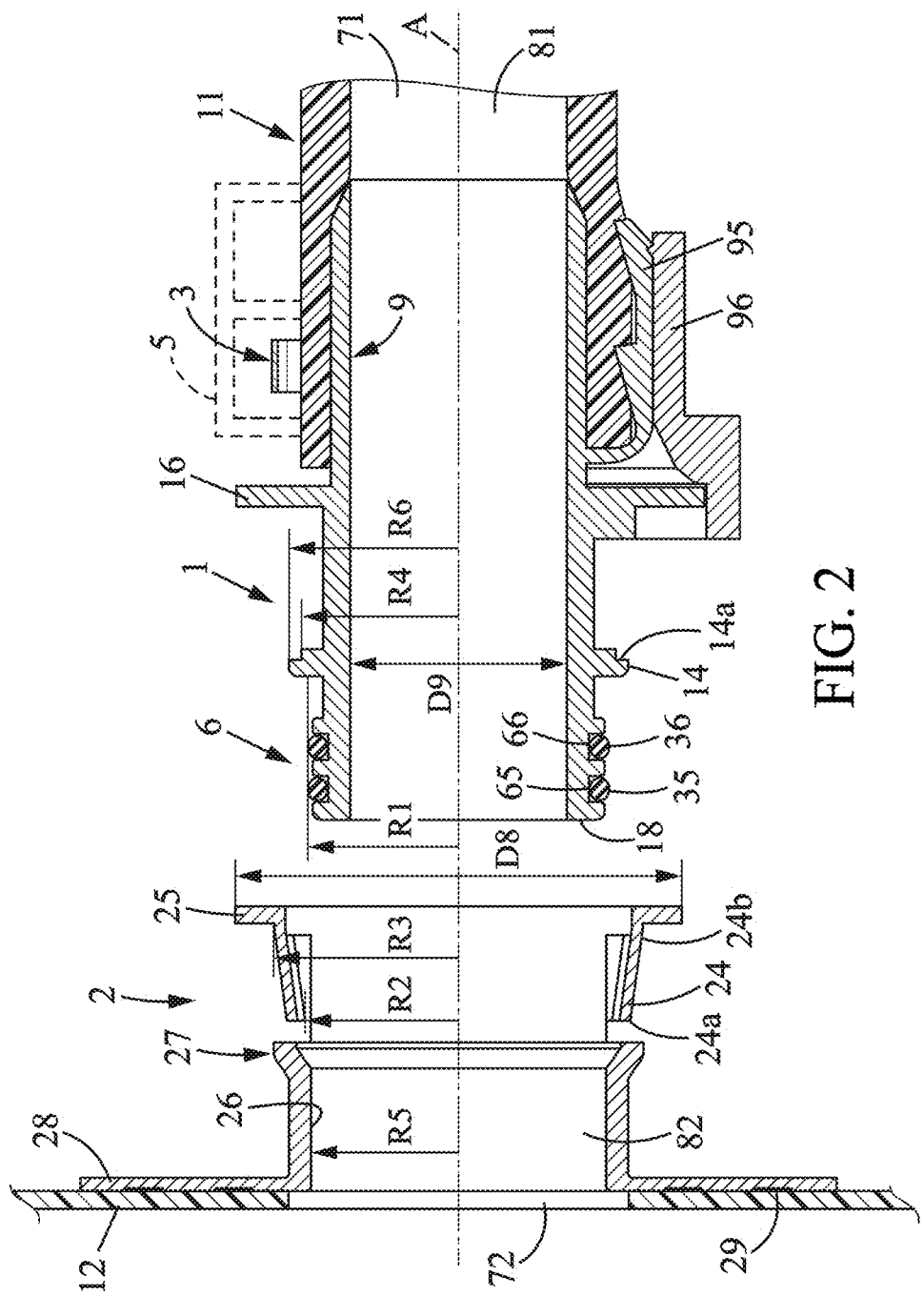
FIG. 2 is an axial sectional view of the connection device of FIG. 1, in the separated position.

In the example illustrated in FIGS. 1-3, a first connector 1 of the male type is to be connected to a second connector 2 of the female type.

In the example illustrated here, the first connector 1 is intended to be connected to a flexible pipe 11 which can be generally defined as a first wall 11 defining a first fluid space 71.

In the example illustrated here, the second connector 2 is intended to be connected to a biopharmaceutical bag 12 which forms a second fluid space 72.

The first connector 1 and the second connector 2 are made of synthetic material, more specifically they can be obtained by molding a plastic material, for example polypropylene, polyethylene, polycarbonate, polysulfone, polyamide, PBT, ABS, or some other similar plastic.

The first connector 1 comprises a male-type connection interface, its general shape symmetrical about axis A, with a front end 18, a first annular groove 65 for receiving a first seal 35, in the current example an O-ring of elastomeric material, and optionally a second annular groove 66 for receiving a second seal 36, in the current example an O-ring of elastomeric material.

The two seals are arranged one after the other in the axial direction A, but in identical radial positions, between the front end 18 and a collar as will be seen below.

When the seal (or seals) is in place in the groove, it occupies a maximum radial dimension denoted R1, as measured from the axis when the seal is in place in the groove but the first connector is not yet inserted into the second connector.

Behind the seals, the male interface further comprises a stop collar 14 also called a snap-fitting collar 14 which has a maximum radial extension denoted R6.

Optionally, the collar 14 may comprise an annular shoulder 14a that extends between an intermediate radial position R4 and the maximum radial extension R6.

The inner diameter of the hollow space 81 defined by the internal cylinder of the first connector is denoted D9.

The first connector 1 further comprises a connection interface with the first fluid space, whether said space is a pipe, a flexible bag, or a filter cartridge. In the example shown, it is a flexible pipe 11 which is inserted onto an endpiece 9 of the first connector.

Two alternative variants for connecting the pipe 11 to the endpiece 9 are illustrated in FIG. 2:

in the upper part of the sectional view of FIG. 2, the pipe 11 is clamped to the endpiece by a conventional ear clamp 3, protected by a protective cover 5 drawn with a dotted line, in the lower part of the sectional view of FIG. 2, the pipe 11 is clamped to the endpiece by integral flexible tabs 95 pressed radially inward by a separate ring 96 which slides axially.

An auxiliary collar 16, larger in size than the first collar 14 already mentioned, can fulfill several functions, such as stopping the sliding ring 96 and optionally snap-fitting with it, serving as gripping elements for a user, and serving as a stop for the pipe insertion. In addition, this auxiliary collar 16 can serve as a stop for the coupling movements, as will be seen below.

The second connector 2 comprises an internal cylinder 26 for receiving the male part, symmetrical about the axis A and having a radius denoted R5. In the coupled position, the seal 35 (and possibly 36) comes to bear with radial compression against this internal cylinder 26 which forms a hollow space 82.

As a result, one will note that to obtain this radial pressure, radius R1 must be slightly greater than radius R5.

In addition, the second connector 2 comprises at least one flexible tongue 24 provided for cooperating with said collar 14 in order to lock the coupling position; in the current example there are two diametrically opposite flexible tongues, each having an attached base 24$b$ and a free end 24$a$ oriented towards the second fluid space, in other words towards the rear of the second connector.

More specifically, during the movement of inserting the male part, the collar 14 spreads the free ends 24$a$ of each flexible tongue radially outward. Once the insertion of the male connector reaches a certain point in its travel, the collar 14 has passed beyond the free ends 24$a$ of the tongues and they are biased by their elasticity to return inward. In this position, the free end of the tongues abuts against the shoulder 14$a$ of the collar 14, which prevents removal of the male part; this snap-fit locks the coupling position. Any other cooperation between contours of the male part and contours of the female part could also be implemented to obtain a similar result.

The second connector 2 also comprises an attachment disc 28 adapted for attachment by welding 29 to a bag 12 or a filter for a biopharmaceutical product. However, the second connector 2 could also be adapted for connection to a second flexible pipe in a manner similar to what was presented for the first connector.

In an advantageous arrangement, the free end 24$a$ of the flexible tongue is distanced from the axis by a second radial distance denoted R2, such that R2>R1, namely the second radial distance R2 is greater than the first radial distance R1. Thus, during the insertion movement, the free end of the tongue cannot damage the O-rings, even if it has a sharp edge.

In an advantageous aspect, the flexible tongue occupies limited space radially; the flexible tongue is circumscribed, relative to the axis, between the second radial distance R2 and a third radial distance R3, which satisfies the relation $1<R3/R2<1.4$.

This provides a particularly compact solution if we compare this third radial distance R3 to the working diameter D9 of the fluid connection.

It should be noted here that the radial distance R4 defines the shoulder 14$a$ against which the end of the flexible tongues rests after passing the snap-fitting collar; this radial distance R4 is greater than the second radial distance R2, such that the flexible tongue does not return fully to its home position and retains a residual radial force directed inward (FIG. 3). This allows accommodating manufacturing tolerances, variations in behavior according to environmental conditions such as humidity, temperature, etc.

As for the snap-fitting collar 14 of the first male connector, it has a maximum radial extension, denoted R6, which satisfies the relation $1<R6/R2<1.3$. The male coupling interface 6 is thus provided in a manner that is very compact radially.

It should be noted here that the auxiliary collar 16 may be absent or have a much smaller diameter, for example similar to that of the collar 14.

In the example in FIGS. 1 to 3, the locking tongues 24 spread apart outwardly when the second collar 14 advances to their free end, then they return inwardly to be positioned on the rear of the second collar 14. After this it is not possible to reverse the movement, in other words to remove the first connector from the second connector, without first spreading apart the locking tongues 24 in some manner, which in practice is impossible to achieve manually and very difficult to achieve with a tool.

However, in the embodiment illustrated in FIG. 4, a release member 25 is provided on each flexible tongue 24, integrally obtained when molding the second connector.

This release member 25 comprises a connecting member 21 connected to the flexible tab, a bearing area 22, and a radial arm 20 arranged between the connecting member and the support area.

The bearing area 22 is intended to be pressed radially inward, for example by an operator's fingers, in order to move the flexible tab 24 radially outward and thus release the locking collar 14 due to the pivoting effect provided by the radial arm 20.

In the variant shown in FIG. 4, the bearing area is directly accessible and can be maneuvered unconditionally.

In contrast, in the case of the variants shown in FIGS. 5 and 6, there is a secondary locking means 23 arranged between the bearing area 22 and the body 27 of the second connector.

According to the variant of FIG. 6, the secondary lock 23 is a radially oriented finger which is movable between an inactive position (as shown) and an active position where it is moved toward the right and is then located under the bearing area 22, forming a prop which prevents movement when pressure is applied to the bearing area 22.

If one wishes to disconnect the fluid connection, first the secondary lock 23 must be eliminated by moving the radially oriented finger to the left and then applying inward radial pressure on the bearing areas 22, allowing removal of the first connector from the second connector.

According to the variant of FIG. 5, a radially oriented finger further comprises a hook that makes it more difficult to undo the secondary lock. In addition, when the secondary lock is undone, this causes damage to the radial finger and generates a permanent indication 23$a$ that the bearing area has been manipulated, possibly the breakage of a mechanical fuse (not shown).

Note that all variants of the second connector presented above share a common basis; the unlocking member 25 may optionally be incorporated depending on the configuration of the molding die. The same is true for the variants of the secondary locking function.

FIG. 7 shows another embodiment in which the second connector 2 comprises two female coupling interfaces arranged head to tail along an axis A; this connector can therefore be called a "double female" connector.

The first female interface 91 is intended to receive the first male connector 1 when coupled. The second female interface 92 is intended to receive a third connector 93 of the male type. The male and female interfaces themselves are identical or similar to what was described above. In particular, the geometry and position of the locking tongues 24,24' are in accordance with what has been described above, to prevent damage to the O-ring by the ends of these locking tongues. Although not shown, the double female connector 2 may also be equipped with the unlocking members and the optional secondary locks described above.

Figure 8B:
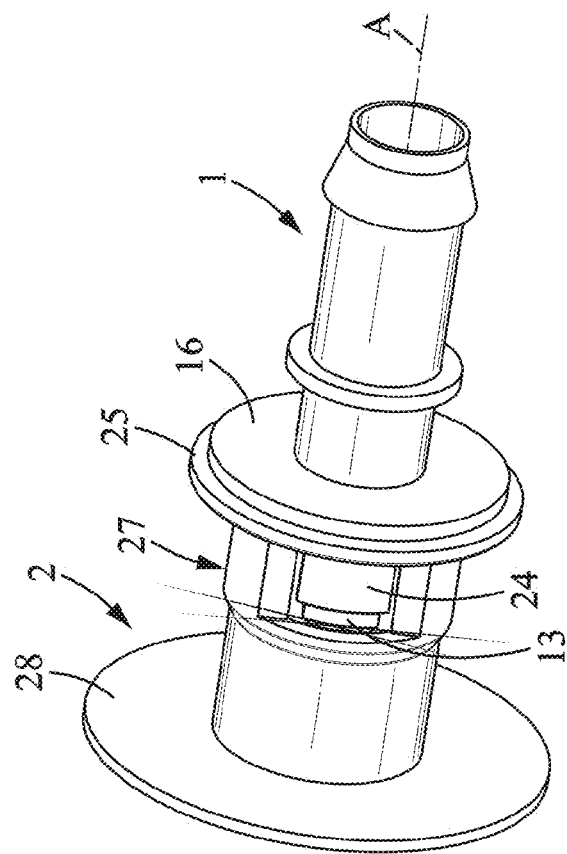
FIGS. 8A and 8B illustrate a variant of the connection device, with an anti-rotation function.
Figure 8A:
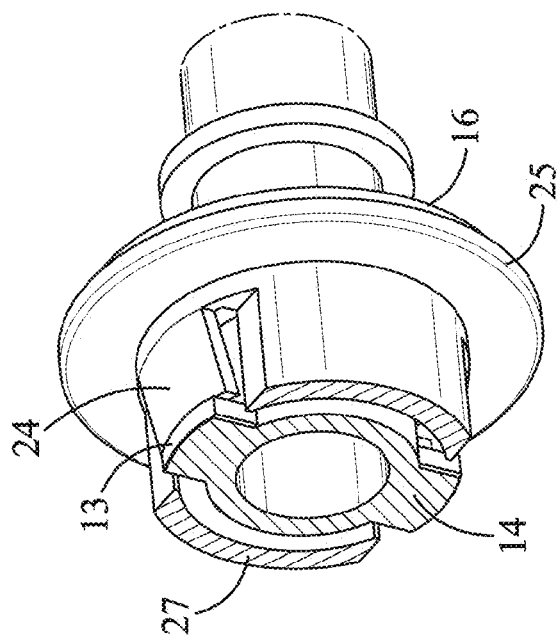

FIGS. 8A and 8B represent an alternative embodiment in which an anti-rotation function is added. Specifically, the snap-fitting collar 14 is reduced to two lugs 13 extending radially outward, each lug being intended to engage with the flexible tongue 24 in the same manner as described above for the cylindrical collar 14.

Since the lugs 13 protrude slightly, this forms an abutment that is tangential to the body 27 of the connector; rotational movement of the first connector relative to the second connector is thus prevented.

In addition, one should note the axial compactness of the male-female coupling with the integrated locking function. Indeed, the axial distance between the snap-fitting collar 14 and the front end 18 of the male connector is less than the working inner diameter D9 of the pipe. In addition, the axial distance between the attachment disc 28 and the base of the flexible tabs 24*b* is less than twice the working inner diameter D9 of the pipe. As a result, both the male connector 1 and the female connector 2 provide optimized axial compactness.

In addition, an optional feature is provided that is compatible with all variants mentioned above: this concerns the integration of an identifier 50, such as a barcode or electronic tag, for example an RFID tag. Preferably, this identifier is provided on the surface of the second connector 2, but in the case of the RFID tag it could be placed anywhere on the first connector 1 and second connector 2, accessible for reading by transponder.

The invention claimed is:

1. A fluid-connection device adapted and intended for connecting a first wall defining a first fluid space to a second wall defining a second fluid space, in a biopharmaceutical assembly, so as to ensure a fluid communication between the first fluid space and the second fluid space, comprising:
   a first connector, defining a first hollow passage, adapted and intended for connection to the first wall and in fluid communication with the first fluid space, the first connector being of the male type, the first connector comprising at least one seal and a snap-fitting collar, the seal extending radially from the axis to a first radial distance R1, this first distance being measured before coupling when the seal is mounted on the first connector; and
   a second connector defining a second hollow passage, adapted and intended for connection to the second wall and in fluid communication with the second fluid space, the second connector being of the female type,
   the first connector and the second connector being adapted and intended to be coupled together in a relative coupling position, along an axis A,
   the second connector comprising at least one flexible tongue with at least one free end against which the snap-fitting collar abuts when in the coupling position, to prevent withdrawal from the coupling position,
   the radially innermost portion of the at least one flexible tongue being distanced from the axis, at rest and prior to insertion, by a second radial distance R2,
   wherein R2>R1, namely the second radial distance R2 is greater than the first radial distance R1,
   wherein the at least one flexible tongue is circumscribed, relative to the axis, between the second radial distance R2 and a third radial distance R3 which satisfies the relation 1<R3/R2<1.4.

2. The connection device according to claim 1, wherein the snap-fitting collar has a maximum radial extension, denoted R6, which satisfies the relation 1<R6/R2<1.3.

3. The connection device according to claim 1, wherein the at least one flexible tongue comprises two flexible tongues that are diametrically opposed.

4. The connection device according to claim 1, comprising two O-rings between the front end of the first connector and the snap-fitting collar.

5. The connection device according to claim 1, wherein the seal is an O-ring or a lip seal of elastomeric material.

6. The connection device according to claim 1, wherein the second connector comprises an additional auxiliary interface of the female type, formed symmetrically with respect to a first interface of the female type, said auxiliary interface being configured to receive a third connector of the male type.

7. A Biopharmaceutical assembly comprising a fluid-connection device according to claim 1.

8. A fluid-connection device adapted and intended for connecting a first wall defining a first fluid space to a second wall defining a second fluid space, in a biopharmaceutical assembly, so as to ensure a fluid communication between the first fluid space and the second fluid space, comprising:
   a first connector, defining a first hollow passage, adapted and intended for connection to the first wall and in fluid communication with the first fluid space, the first connector being of the male type, the first connector comprising at least one seal and a snap-fitting collar, the seal extending radially from the axis to a first radial distance R1, this first distance being measured before coupling when the seal is mounted on the first connector; and
   a second connector defining a second hollow passage, adapted and intended for connection to the second wall and in fluid communication with the second fluid space, the second connector being of the female type,
   the first connector and the second connector being adapted and intended to be coupled together in a relative coupling position, along an axis A,
   the second connector comprising at least one flexible tongue with at least one free end against which the snap-fitting collar abuts when in the coupling position, to prevent withdrawal from the coupling position,
   the radially innermost portion of the at least one flexible tongue being distanced from the axis, at rest and prior to insertion, by a second radial distance R2,
   wherein R2>R1, namely the second radial distance R2 is greater than the first radial distance R1,
   wherein each flexible tongue is connected to an unlocking member that is integrally obtained when molding the second connector, and which comprises a connecting member joined to the flexible tongue, a bearing area, a radial arm arranged between the connecting member and the bearing area, the bearing area being intended to be pressed radially inward to urge the flexible tongue radially outward and thereby release the snap-fitting collar.

9. A Biopharmaceutical assembly comprising a fluid-connection device according to claim 8.

10. The connection device according to claim 8, wherein the unlocking member comprises a secondary locking means for the bearing area, to prevent radially inward movement of the bearing area, thus doubly locking the connection.

11. The connection device according to claim 10, wherein the secondary locking means forms an indicator of an unlocking attempt and may comprise a mechanical fuse region.

12. The connection device according to claim 8, wherein the secondary locking means is a radially-oriented finger which is movable between an inactive position and an active position.

13. A fluid-connection device adapted and intended for connecting a first wall defining a first fluid space to a second wall defining a second fluid space, in a biopharmaceutical assembly, so as to ensure a fluid communication between the first fluid space and the second fluid space, comprising:
    a first connector, defining a first hollow passage, adapted and intended for connection to the first wall and in fluid communication with the first fluid space, the first connector being of the male type, the first connector comprising at least one seal and a snap-fitting collar, the seal extending radially from the axis to a first radial distance R1, this first distance being measured before coupling when the seal is mounted on the first connector; and
    a second connector defining a second hollow passage, adapted and intended for connection to the second wall and in fluid communication with the second fluid space, the second connector being of the female type,
    the first connector and the second connector being adapted and intended to be coupled together in a relative coupling position, along an axis A,
    the second connector comprising at least one flexible tongue with at least one free end against which the snap-fitting collar abuts when in the coupling position, to prevent withdrawal from the coupling position,
    the radially innermost portion of the flexible tongue being distanced from the axis, at rest and prior to insertion, by a second radial distance R2,
    wherein R2>R1, namely the second radial distance R2 is greater than the first radial distance R1,
    wherein the collar comprises an anti-rotation lug which extends radially beyond the rest of the collar.

14. A Biopharmaceutical assembly comprising a fluid-connection device according to claim 13.

15. A fluid-connection device adapted and intended for connecting a first wall defining a first fluid space to a second wall defining a second fluid space, in a biopharmaceutical assembly, so as to ensure a fluid communication between the first fluid space and the second fluid space, comprising:
    a first connector, defining a first hollow passage, adapted and intended for connection to the first wall and in fluid communication with the first fluid space, the first connector being of the male type, the first connector comprising at least one seal and a snap-fitting collar, the seal extending radially from the axis to a first radial distance R1, this first distance being measured before coupling when the seal is mounted on the first connector, and
    a second connector defining a second hollow passage, adapted and intended for connection to the second wall and in fluid communication with the second fluid space, the second connector being of the female type,
    the first connector and the second connector being adapted and intended to be coupled together in a relative coupling position, along an axis A,
    the second connector comprising at least one flexible tongue with at least one free end against which the snap-fitting collar abuts when in the coupling position, to prevent withdrawal from the coupling position,
    said snap-fitting collar, when in the coupling position, abutting against said one free end of said flexible tongue and pushing against said one free end of said flexible tongue in a direction from the second fluid space toward the first fluid space, to prevent withdrawal from the coupling position,
    the radially innermost portion of each flexible tongue being distanced from the axis, at rest and prior to insertion, by a second radial distance R2,
    wherein R2>R1, namely the second radial distance R2 is greater than the first radial distance R1,
    wherein each flexible tongue has a free end oriented toward the second fluid space,
    wherein the first connector or the second connector further comprises an identifier, and
    wherein the identifier is a barcode.

16. A Biopharmaceutical assembly comprising a fluid-connection device according to claim 15.

17. A fluid-connection device adapted and intended for connecting a first wall defining a first fluid space to a second wall defining a second fluid space, in a biopharmaceutical assembly, so as to ensure a fluid communication between the first fluid space and the second fluid space, comprising:
    a first connector, defining a first hollow passage, adapted and intended for connection to the first wall and in fluid communication with the first fluid space, the first connector being of the male type, the first connector comprising at least one seal and a snap-fitting collar, the seal extending radially from the axis to a first radial distance R1, this first distance being measured before coupling when the seal is mounted on the first connector, and
    a second connector defining a second hollow passage, adapted and intended for connection to the second wall and in fluid communication with the second fluid space, the second connector being of the female type,
    the first connector and the second connector being adapted and intended to be coupled together in a relative coupling position, along an axis A,
    the second connector comprising at least one flexible tongue with at least one free end against which the snap-fitting collar abuts when in the coupling position, to prevent withdrawal from the coupling position,
    said snap-fitting collar, when in the coupling position, abutting against said one free end of said flexible tongue and pushing against said one free end of said flexible tongue in a direction from the second fluid space toward the first fluid space, to prevent withdrawal from the coupling position,
    the radially innermost portion of each flexible tongue being distanced from the axis, at rest and prior to insertion, by a second radial distance R2,
    wherein R2>R1, namely the second radial distance R2 is greater than the first radial distance R1,
    wherein each flexible tongue has a free end oriented toward the second fluid space,
    wherein the first connector or the second connector further comprises an identifier, and
    wherein the identifier is an RFID tag.

18. A Biopharmaceutical assembly comprising a fluid-connection device according to claim 17.

* * * * *